United States Patent [19]

Sundberg et al.

[11] Patent Number: 4,803,157

[45] Date of Patent: Feb. 7, 1989

[54] HYDROLYZABLE FLUORESCENT SUBSTRATES FOR PHOSPHATASES AND ANALYTICAL USE THEREOF

[75] Inventors: Michael W. Sundberg, Penfield; Bruce Babb; Gregory McClune, both of Rochester, all of N.Y.

[73] Assignee: Eastman Kodak Company, Rochester, N.Y.

[21] Appl. No.: 824,752

[22] Filed: Jan. 31, 1986

[51] Int. Cl.[4] ............................ F12Q 1/42; C07F 9/02
[52] U.S. Cl. ............................... 435/21; 260/502.5 R; 435/7; 436/800; 558/210
[58] Field of Search ...................... 435/7, 21; 436/800; 260/502.5 R; 558/210

[56] References Cited

U.S. PATENT DOCUMENTS

| | | | |
|---|---|---|---|
| 4,051,175 | 9/1977 | Andrew et al. | 260/502.5 R |
| 4,279,992 | 7/1981 | Boguslaski et al. | 435/7 |
| 4,476,229 | 10/1984 | Fino et al. | 436/800 |

FOREIGN PATENT DOCUMENTS 122148  10/1984  European Pat. Off. .

OTHER PUBLICATIONS

Koller et al., *Anal. Biochem.*, 143, pp. 146–151 (1984).
Cooke et al., *Aust. J. Chem.*, 11, pp. 230–235 (1958).
Solodar et al., *Zhrir. Organ. Khimii*, 16 (5), pp. 1062–1064 (1980).

*Primary Examiner*—Sam Rosen
*Attorney, Agent, or Firm*—J. L. Tucker

[57] ABSTRACT

Hydrolyzable substrates for acid and alkaline phosphatases comprise blocked dye moieties which, when cleaved from the substrate during hydrolysis, provide fluorescent dyes having maximum absorptions above about 530 nm and maximum fluorescent emissions at least about 580 nm. The dyes are blocked prior to hydrolysis with a phosphono or thioxophosphono group or a salt thereof. These substrates can be used in analytical determinations of acid or alkaline phosphatase, or in competitive binding reactions to determine immunologically reactive substances.

16 Claims, No Drawings

HYDROLYZABLE FLUORESCENT SUBSTRATES FOR PHOSPHATASES AND ANALYTICAL USE THEREOF

CROSS-REFERENCE TO RELATED APPLICATIONS

Reference is made to the following copending and commonly assigned applications:

U.S. Ser. No. 824,757, filed on even date herewith by Babb et al and entitled BIOLOGICAL AND ANALYTICAL USES OF PHENALENONE AND BENZPHENALENONE COMPOUNDS, U.S. Ser. No. 824,756, filed on even date herewith by Babb et al and entitled HYDROLYZABLE FLUORESCENT SUBSTRATES AND ANALYTICAL DETERMINATIONS USING SAME, and U.S. Ser. No. 824,755, filed on even date herewith by Wu and entitled USE OF POLYMERIC MORDANTS TO INCREASE THE INTENSITY OF RIGID FLUORESCENT DYES.

This invention relates to clinical chemistry and the determination of acid or alkaline phosphatase. It particular, it relates to hydrolyzable fluorescent substrates for phosphatases. It also relates to both dry and wet analytical methods for the determination of phosphatases, or of immunologically reactive substances.

BACKGROUND OF THE INVENTION

The quantitative determination of acid or alkaline phosphatase and isoenzymes thereof in biological fluids, and particularly in human blood serum, has become very important in the diagnosis and treatment of various physical disorders. Acid phosphatase (ACP) refers to a group of phosphatases with optimal activity below pH 7.0 that catalyze the hydrolysis of many orthophosphoric monoesters. ACP is present in most tissues with the prostate gland having the highest concentration. Increased serum levels of ACP can indicate a number of disease states especially prostate cancer.

Alkaline phosphatase (ALP) refers to a group of nonspecific phosphatases that exhibit optimal activity at alkaline pH. Determination of alkaline phosphatase is very important in the detection of bone and liver diseases. For example, elevated alkaline phosphatase concentrations are often associated with Paget's disease, osteosarcomas, osteomalacia, obstructive jaundice, hepatitis and the like. An early and rapid detection of elevated phosphatase concentrations can then lead to rapid treatment of the causative conditions. As a result, various assay procedures have been developed over the years to provide a quantitative determination of acid or alkaline phosphatase.

A number of analytical procedures have been developed whereby a substrate is hydrolyzed by an enzyme of interest to relase a detectable moiety. These procedures use both colorimetric and fluorometric methods. Fluorometric assays are preferred because of generally greater sensitivity. However, known fluorometric assays are deficient in a number of ways. For example, E.P. Application No. 122,148 (published Oct. 17, 1984) describes an assay for microorganisms using certain coumarin derivatives as substrates which release fluorescent dyes when the substrate is hydrolyzed. The coumarin dyes can be attached to a sugar radical, alcohol radical or a phosphate radical. However, the dyes of this reference have absorption and emission spectra in regions subject to spectral interference from hemoglobin and bilirubin.

A preferred substrate for alkaline phosphatase is p-nitrophenylphosphate which, upon hydrolysis at pH 9.8–10.5, releases p-nitrophenol, which has a maximum absorption at about 400 nm. A number of serum components also absorb in that region of the spectrum.

A preferred substrate for acid phosphatase is thymolphthalein monophosphate which, upon hydrolysis at pH 5.4, releases thymolphthalein which has maximum absorption at about 595 nm. However, alkali must be added to the assay to raise the pH to alkaline values prior to measuring the spectrophotometric signal.

Recently, an acid phosphatase assay was described using improved umbelliferone derivatives (Koller et al, Anal. Biochem., 143, pp. 146-151, 1984). However, the dyes described therein absorb at wavelengths at about 500 nm or below, i.e. in the region of absorption of serum components bilirubin and hemoglobin.

It would be desirable to have substrates which are not subject to the problems of known assays.

SUMMARY OF THE INVENTION

The present invention overcomes the problems noted above with hydrolyzable compounds represented by the formula:

BLOCK—X—R<sup>f</sup>—L 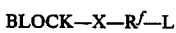

wherein BLOCK is phosphono, thioxophosphono [—P(S)—(OH)₂] or a salt thereof, X is —O—, —S— or —NR— wherein R is hydrogen or substituted or unsubstituted alkyl, provided that when BLOCK is thioxophosphono or a salt thereof, X is —O—, R<sup>f</sup> is a substituted or unsubstituted phenalenone or benzphenalenone moiety provided that when released as —X—R<sup>f</sup>—L, —X—R<sup>f</sup>—L exhibits maximum fluorescence emission at least about 580 nm and maximum absorption above about 530 nm, and L is hydrogen or a specific binding ligand.

An analytical composition of this invention comprises an aqueous solution buffered to a pH of 12 or less containing the hydrolyzable compound described above.

Further, this invention provides an analytical element comprising an absorbent carrier material and containing the hydrolyzable compound described above.

Still further, a method for the determination of acid or alkaline phosphatase comprises the steps of:

A. under hydrolyzing conditions, contacting a sample of a liquid suspected of containing a phosphatase with the hydrolyzable compound described above, and B. determining the fluorescent moiety released from the compound by hydrolysis as a result of the presence of the phosphatase at a wavelength at least about 580 nm after excitation at a wavelength above about 530 nm.

The present invention provides novel substrates for acid and alkaline phosphatases which release fluorescent dyes when the substrates are hydrolyzed. Advantageously, the released dyes absorb and emit radiation away from spectral interferents commonly encountered in biological fluids. Further, the fluorescence excitation and emission spectra of the released dyes are shifted, i.e. they are different from those of the substrates themselves.

The assay of this invention which uses the substrates noted above is rapid and highly sensitive. It can be used to advantage to determine either acid or alkaline phosphatase in biological fluids. It can also be used to determine an immunologically reactive substance when either acid or alkaline phosphatase is used as the label, or when the hydrolyzable compound describe above is used as the label.

DETAILED DESCRIPTION OF THE INVENTION

The present invention can be used to qualitatively or quantitatively determine phosphatases. The invention can be used to determine a single isoenzyme of a phosphatase, or it can be used to determine total acid or alkaline phosphatase activity. The substrates of this invention can be used in analytical determinations of any aqueous liquids which are suspected of containing a phosphatase. The invention is preferably used to assay biological fluids, e,g, urine, blood serum, whole blood, spinal fluid, etc. The substrates of this invention can also be used in specific binding assays, i.e. in enzyme immunoassays, where the enzymes, ACP or ALP, are used as the labels, or in substrate-labeled immunoassays, where the substrates are used as labels as described in more detail below. The determinations can be made via a single reaction or a sequence of reactions initiated by acid or alkaline phosphatase which brings about hydrolysis of the substrate and release of the fluorescent dye.

The substrates of this invention are represented by the formula:

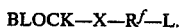

In this formula, BLOCK represents a phosphono group, thioxophosphono group [—P(S)—(OH)$_2$] or a salt thereof (e.g. magnesium, sodium, potassium, tris(hydroxyethyl)methyl ammonium, cyclohexylammonium, etc.) which can be cleaved from the remainder of the molecule by hydrolysis at a pH of 12 or less. Preferably, BLOCK is a phosphono group. The salts are generally more stable than the free acid substrates in aqueous solutions.

When BLOCK is phosphono or a salt thereof, X is oxy, thio or imino (—NR—) wherein R is hydrogen or substituted or unsubstituted alkyl, preferably of 1 to 5 carbon atoms (e.g. methyl, ethyl, propyl, isopropyl, t-butyl, etc.). Preferably, X is oxy or imino wherein R is hydrogen. When BLOCK is thioxophosphono or a salt thereof, X is oxy only.

R$^f$ is a moiety derived from a substituted or unsubstituted phenalenone or benzphenalenone fluorescent compound. When BLOCK is cleaved from the remainder of the molecule by hydrolysis, the resulting hydrolyzed moiety (i.e. —X—R$^f$—L) exhibits maximum fluorescence at a wavelength at least about 580 nm when excited at a wavelength above about 530 nm.

Useful phenalenone or benzphenalenone fluorescent moieties are selected from the group consisting of

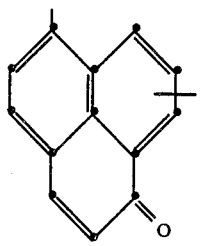

and

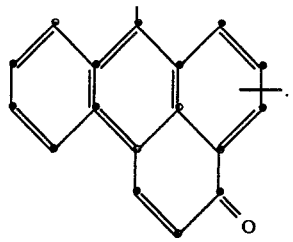

Representative fluorescent compounds from which the fluorescent moieties are derived include:

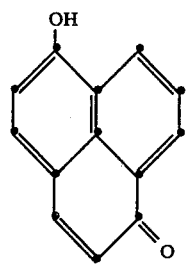

I.

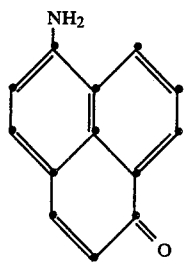

II.

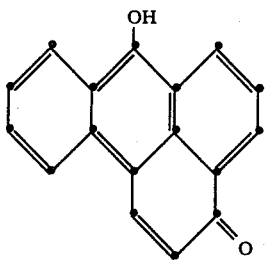

III.

and

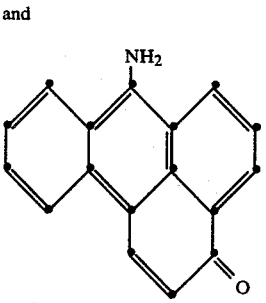

IV.

Compounds I and II are particularly useful in the practice of this invention.

These fluorescent moieties can contain one or more other substituents which do not adversely affect their fluorescence or hydrolytic properties at one or more positions on one or more of the fused rings. Such substituents include substituted or unsubstituted alkyl (preferably of 1 to 12 carbon atoms, e.g. methyl, ethyl, benzyl, etc.), substituted or unsubstituted hydroxyalkyl (preferably of 1 to 12 carbon atoms, e.g. hydroxymethyl, 2-hydroxyethyl, etc.), substituted or unsubstituted alkoxycarbonyl (preferably of 2 to 12 carbon atoms, e.g. methoxycarbonyl, ethoxycarbonyl, etc.), halo (e.g. fluoro, chloro, bromo), cyano carboxy, acyl, substituted or unsubstituted arylsulfonyl (preferably of 6 to 10 carbon atoms, e.g. phenylsulfonyl, tolylsulfonyl, etc.), substituted or unsubstituted alkylsulfonyl (preferably of 1 to 6 carbon atoms, e.g. methylsulfonyl, ethylsulfonyl, etc.), and other substituents known to one skilled in the art.

Fluroescent compound I identified above can be prepared by the method described by Cooke et al in *Australian J. Chem.*, 11, pp. 203–235 (1958). Fluorescent compound II can be prepared by the method described by Solodar et al in *Zhurnal Organcheskoi Khimii* 16(5), pp. 1062–1064 (1980). Fluorescent compound III is prepared by the procedure described in U.S. Ser. No. 824,757 of Babb et al noted above. Fluorescent compound IV can be prepared by procedures similar to those described by Solodar et al noted above.

Generally, the substrates of this invention are prepared by the following steps: (1) the preparation of the phenalenone or benzphenalenone compound and (2) reaction of the dye with phosphoryl chloride or thiophosphoryl chloride to form the blocked substrate. The blocked dye can then be reacted with an appropriate metal reagent to form a salt. A representative preparation is provided in Example 1 below.

In the formula shown above, L is preferably hydrogen. However, L can also be a specific binding ligand so that the substrate can be used in a substrate-labeled fluorescent immunoassay as described for example in U.S. Pat. No. 4,279,992 (issued July 21, 1981 to Boguslaski et al). In such assays, the analyte to be determined is a ligand which will complex with a specific receptor. The assay is based on using a label that is a fluorogenic enzyme substrate. When the label is hydrolyzed by acid or alkaline phosphatase, it yields a detectable fluorescent product. In the present invention, the fluorescent product (phenalenone or benzphenalenone) advantageously absorbs at a wavelength above about 530 nm and fluoresces at a wavelength at least about 580 nm. Binding of the labeled ligand by the receptor prevents the enzyme from hydrolyzing the substrate. Since a fluorescent product will not be produced by antibody-bound label, bound label can be distiguished from unbound label.

The assay can be used for the determination of any specific binding ligand, particularly haptens, such as drugs, and antibodies, antigens, hormones, polypeptides, etc. The substrates can also be used in what are known in the art as "sandwich" assays.

When L is a specific binding ligand, it is attached to $R^f$ by a covalent linking group. It will be recognized that there are many methods for covalently linking the ligand to $R^f$. The particular chemical character of the linking group will depend upon the nature of the respective available linking sites on the ligand and $R^f$. Selection of the linking group depends upon preservation of the ability of the ligand to participate in the specific binding reaction and the retention of absorption and emission properties. Generally, the linking group comprises a single or a double bond, or a chain containing between 1 and 10 carbon or heteroatoms in the chain.

Particular examples of useful linking groups and methods of preparing —$R^f$—L are described in U.S. Pat. No. 4,279,992 noted above.

Depending upon their water solubilities, the substrates of this invention can be either dissolved directly in buffers or in a combination of buffer and water-miscible organic solvents, or dispersions can be prepared containing a substrate, buffer, water-miscible organic solvent and surfactant.

In the determination of acid or alkaline phosphatase, an analytical composition is generally buffered at pH 12 or less with one or more appropriate buffers. Generally, when alkaline phosphatase is to be determined, the pH is kept in the range of from about 8 to about 11, and preferably at about pH 10. When acid phosphatase is to be determined, the pH is kept in the range of from about 6 to about 7, and preferably at about pH 6. Useful buffers are readily determined by one skilled in the art and include phosphates, borates, carbonates and organic buffers as reported by Good et al in *Biochem.* 5, 467 (1966) and *Anal. Biochem.* 104, 300 (1980).

Surfactants which are useful in the practice of this invention include any surfactants which do not inhibit hydrolysis. Useful surfactants are generally nonionic and include alkylarylpolyethoxy alcohols (e.g. TRITON X-100 and X-305 available from Rohm & Haas, Philadelphia, Pa., p-alkylaryloxypolyglycidols (e.g. SURFACTANT 10G available from Olin Corp., Stamford, Conn.), TWEEN 80 (available from ICI Americas, Inc., Wilmington, Del.), and others known to one skilled in the art.

Useful water-miscible organic solvents include alcohols (e.g. methanol, ethanol, propanol, etc.), N,N-dimethylformamide, dimethyl sulfoxide, acetonitrile, hexamethylenephosphoramide and the like. The particular solvent to be used can be readily determined by routine experimentation.

A solution of the substrate can be prepared in the following general manner. The substrate is dissolved in the water-miscible solvent at a concentration which depends upon its molecular weight, but generally at from about 1 to about 100, and preferably from about 5 to about 80, mg per ml of solvent. The resulting solution is then mixed with a suitable surfactant in an amount generally of from about 0.1 to about 24, and preferably from about 0.5 to about 10, mg surfactant per ml of solution then added to the appropriate buffer solution. This preparation is generally carried out at room temperature.

The buffer is present in an amount effective to maintain the desired pH (12 or less). The concentration of buffer in the dispersion can vary widely, but is generally from about 0.01 to about 0.5 molar. Representative buffers are described above.

The present invention is adaptable to either solution or dry assays. In a solution assay, a solution (or aqueous dispersion) containing a substrate can be prepared and contacted by mixing with a liquid test sample containing acid or alkaline phosphatase or the ligand to be determined. Generally the substrate is mixed with the test sample in a suitable container (e.g. test tube, petri dish beaker, cuvette, test device, etc.). The resulting solution (or dispersion) is gently mixed and incubated for a relatively short time (i.e. up to about 30 minutes) at a temperature up to about 40° C., and generally from about 20° to about 40° C. The test sample is then evaluated by measuring the resulting fluorescent dye with suitable detection equipment at a wavelength greater than about 580 nm.

The solution assay can also be carried out by contacting a porous absorbent material, e.g. paper strip, containing the test sample with a dispersion of the substrate. The analyte in the test sample can migrate from the porous material into the dispersion and initiate the analytical reactions needed for determination.

In solution assays, the amount of substrate present is at least about 0.01, and preferably from about 10 to about 100, millimolar. Other reagents needed for the assay can be present in amounts readily determined by one skilled in the art.

Alternatively, the method of this invention can be practiced using a dry analytical element. Such an element can be an absorbent carrier material, i.e. a thin sheet or strip of self-supporting absorbent or bibulous material, such as filter paper or strips, which contains the hydrolyzable substrate or a dried residue of a solution or dispersion comprising same. Such elements are known in the art as test strips, diagnostic elements, dip sticks, diagnostic agents and the like.

When employed in dry analytical elements, the substrate can be incorpoated into a suitable absorbent carrier material by imbibition or impregnation, or can be coated on a suitable absorbent carrier material. Alternatively, the substrate can be added to the element during an assay. Useful carrier materials are insoluble and maintain their structural integrity when exposed to water or physiological fluids such as urine or serum. Useful carrier materials can be prepared from paper, porous particulate structures, cellulose, porous polymeric films, wood, glass fibers, woven and nonwoven fabrics (synthetic and nonsynthetic) and the like. Useful materials and procedures for making such elements are well known in the art as exemplified by U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued June 2, 1981 to Kondo et al), and U.K. Patent No. 2,052,057 (published Jan. 21, 1981).

A dry assay can be practiced to particular advantage with an analytical element comprising a support having thereon at least one porous spreading zone as the absorbent carrier material. The substrate can be in the spreading zone or in a different zone (e.g. reagent zone, registration zone, hydrophilic zone, etc.). The spreading zone can be prepared from any suitable fibrous or nonfibrous material or mixtures of either or both.

The spreading zone can be prepared using fibrous materials, either mixed with a suitable binder material or woven into a fabric, as described in U.S. Pat. No. 4,292,272 (issued September 29, 1981 to Kitajima et al) or from polymeric compositions (e.g. blush polymers) or particulate materials, with or without binding adhesives, as described in U.S. Pat. Nos. 3,992,158 (issued Nov. 16, 1976 to Przybylowicz et al) 4,258,001 (issued Mar. 24, 1981 to Pierce et al) and 4,430,436 (issued Feb. 7, 1984 to Koyama et al) and Japanese Patent Publication No. 57(1982)-101760 (published June 24, 1982). It is desirable that the spreading zone be isotropically porous, meaning that the porosity is the same in each direction in the zone as created by interconnected spaces or pores.

The dry analytical element of this invention preferably comprises a suitable nonporous support carrying the absorbent carrier material. Such a support can be any suitable dimensionally stable, and preferably, transparent (i.e. radiation transmissive) film or sheet material which transmits electromagnetic radiation of a wavelength between about 200 and about 900 nm. A support of choice for a particular element should be inert to chemical reagents and liquid samples used in the assay. Useful support materials include polystyrene, polyesters [e.g. poly(ethylene terephthalate)], polycarbonates, cellulose esters (e.g. cellulose acetate), etc.

The elements can have more than one zone, e.g. a reagent zone, a registration zone, subbing zone, etc. The zones are generally in fluid contact with each other, meaning that fluids, reagents and reaction products can pass between superposed regions of adjacent zones. Preferably, the zones are separately coated superposed layers, although two or more zones can be located in a single layer. Suitable element formats and components are described also in U.S. Pat. Nos. 4,042,335 (issued Aug. 16, 1977 to Clement) and 4,144,306 (noted above) and U.S. Pat. No. Re. 30,267 (reissued May 6, 1980 to Bruschi).

In the elements of this invention, the amount of the substrate can be varied widely, but it is generally present in a coverage of at least about 0.01, and preferably from about 0.05 to about 1, $g/m^2$. Optional, but preferred reagents are generally present in the following coverages:

buffer: generally at least about 0.1 and preferably from about 0.5 to about 2, $g/m^2$, and surfactant: generally at least about 0.1, and preferably from about 0.2 to about 5, $g/m^2$.

One or more of the zones can contain a variety of other desirable, but optional, components, including activators, binders (generally hydrophilic), coupler solvents, etc. as is known in the art, as well as any reagents needed for assay of acid or alkaline phosphatase or a ligand.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, an analyte or ligand determination is made by taking the element from a supply roll, chip packet or other source and physically contacting it with a sample (e.g. 1–200 $\mu l$) of the liquid to be tested. Such contact can be accomplished in any suitable manner, e.g. dipping or immersing the element into the sample or, preferably, by spotting the element by hand or machine with one or more drops of the sample with a suitable dispensing means. This contact causes the liquid sample to be mixed within the element with the substrate and any other reagents therein.

After sample application, the element is exposed to any conditioning, such as incubation, heating or the like, that may be desirable to quicken or otherwise facilitate obtaining a test result.

Generally, the assay (solution or dry) is carried out under conditions that promote hydrolysis of the substrate by a phosphatase. Such hydrolyzing conditions include conditions of pH and temperature which are conducive to hydrolysis. Generally, the pH will be less than 12, and will depend upon which phosphatase is being determined. The temperature is not critical but is generally up to about 50° C.

Detection of acid or alkaline phosphatase is achieved when the substrate is hydrolyzed releasing a fluorescent moiety which can be detected in a suitable manner at a wavelength at least about 580 nm. It is not necessary, however, for the determination to be made at the wavelength of maximum fluorescence. Determination can be either a rate determination or an end-point determination.

In the case of determination of a specific binding ligand, the released fluorescent dye is related to the amount of ligand in the test sample.

In the examples which follow illustrating the practice of the invention, the materials used were obtained as follows:

TRIS buffer [tris(hydroxymethyl)aminomethane], calf intestine and beef liver alkaline phosphatase (Sigma Chemical Co., St. Louis, Mo., U.S.A.), and the remainder from Eastman Kodak Co. (Rochester, N.Y., U.S.A.) or prepared using available starting materials and known procedures.

As used in the context of this disclosure and the claims, I.U. represents the International Unit for enzyme activity defined as one I.U. being the amount of enzyme activity required to catalyze the conversion of 1 $\mu$mole of substrate per minute under standard pH and temperature conditions for the enzyme.

EXAMPLE 1

PREPARATION OF PHENALENONE-6-PHOSPHATE AND SALTS

6-Hydroxyphenalenone was prepared according to the method described by Cooke et al in the *Austral. J. Chem.* 11, pp. 230–235 (1958). 6-Hydroxyphenalenone (10 g), was dispersed in dry pyridine (150 ml). Phosphorous oxycholoride (10 ml) was added to give a clear, yellow-green solution which was allowed to stand at room temperature for a few minutes to insure complete reaction. It was then poured into 300 ml of cold water. Sodium hydroxide solution (50%) was added to bring the pH up to 9. Most of the pyridine was removed with a rotary evaporator, and the resulting dark orange solution was made acidic with concentrated hydrochloric acid and chilled in an ice/methanol bath. The free acid was collected by filtration, washed with dilute hydrochloric acid and acetone, then redissolved in TRIS buffer to obtain a solution of the TRIS salt of the substrate.

The free acid was also converted to its magnesium salt by first dissolving the free acid in a dilute solution of sodium acetate. Then a solution of magnesium sulfate (15 g) in water (50 ml) was added, and the resulting mixture was filtered to remove a small quantity of dark colored impurity. The clear filtrate was chilled overnight in a freezer. The resulting orange product was filtered off and washed with a small quantity of ice water. The yield was 8 g of phenalenone-6-phosphate magnesium salt having a nuclear magnetic resonance spectrum consistent with the structure.

EXAMPLE 2

KINETIC STUDY OF ALKALINE PHOSPHATASE WITH A SUBSTRATE OF THIS INVENTION

The magnesium salt substrate prepared in Example 1 was used to determine reaction rates and kinetic parameters for alkaline phosphatase at 540 nm. The study was done by using the substrate (concentration range 0.1 mmolar to 10 mmolar), calf intestine alkaline phosphatase (0.01 I.U./ml), sodium carbonate (100 mmolar, pH 10), magnesium chloride (1 mmolar) and zinc perchlorate (1 mmolar). From the data obtained, a double reciprocal plot was drawn. The Michaelis constant (Km) calculated from this plot, was 1.4 mmolar. The rate of reaction (Vmax) was calculated to be 0.029 absorbance (A) units/minute. These values compare well with those obtained with known ALP substrate, p-nitrophenylphosphate tested under the same conditions: Km=1.2 mmolar and Vmax=0.035 A/minute. These data indicate that the phenalenone phosphate of this invention is an excellent substrate for ALP.

EXAMPLE 3

SOLUTION ASSAY FOR ALKALINE PHOSPHATASE

A solution was prepared using the substrate of Example 1 ($10^{-5}$ molar), magnesium acetate ($10^{-0}$ molar) and TRIS buffer (0.1 molar, pH 8.5). One milliliter of this solution was placed in each of two test cells. To one cell was added beef liver ALP (100 $\mu$l, $10^{-5}$ molar). No ALP was placed in the second cell.

The relative fluorescence of the solution in the test cell containing the ALP-hydrolyzed substrate was measured at an excitation of 535 nm and an emission of 580 nm. A rapid generation of fluorescence was observed. Minimal fluorescence was observed at these wavelengths for the second containing unhydrolyzed substrate.

The relative fluorescence of the unhydrolyzed substrate in the second test cell was measured at an excitation of 451 nm and an emission of 535 nm. Minimal fluorescence was observed at these wavelengths for the hydrolyzed substrate in the first test cell.

This example illustrates that the substrate of this invention is hydrolyzed by ALP to produce a shifted fluorescent moiety, whose fluorescence emission can be detected at 580 nm when excited at 535 nm, and thus can be used in an assay for ALP.

The invention has been described in detail with particular reference to preferred embodiments thereof, but it will be understood that variations and modifications can be effected within the spirit and scope of the invention.

We claim:

1. A hydrolyzable compound represented by the formula:

BLOCK—X—R<sup>f</sup>—L wherein BLOCK is phosphono, thioxophosphono or a salt thereof, X is —O—, —S— or —NR— wherein R is hydrogen or alkyl, provided that when BLOCK is thioxophosphono, X is —O—, R<sup>f</sup> is a phenalenone or benzphenalenone moiety selected from the group consisting of

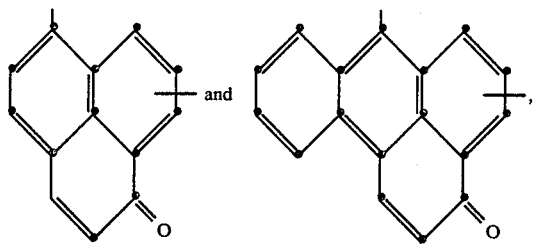 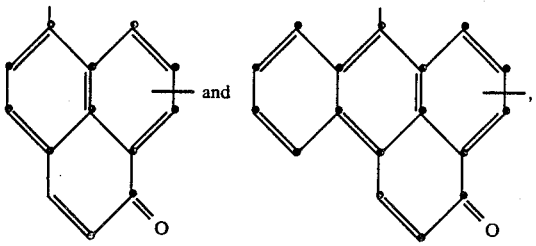

provided that when released as —X—R$^f$—L, —X—R$^f$—L exhibits maximum fluorescent emission at least about 580 nm and maximum absorption above about 530 nm, and L is hydrogen or a specific binding ligand.

2. The compound of claim 1 wherein BLOCK is phosphono.

3. The compound of claim 1 wherein X is —O—.

4. The compound of claim 1 wherein L is hydrogen.

5. The compound of claim 1 wherein L is a specific binding ligand.

6. An analytical composition comprising an aqueous solution buffered to a pH of 12 or less containing a hydrolyzable compound represented by the formula:

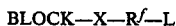

wherein BLOCK is phosphono, thioxophosphono or a salt thereof, X is —O—, —S— or —NR— wherein R is hydrogen or alkyl, provided that when BLOCK is thioxophosphono, X is —O—, R$^f$ is a phenalenone or benzphenalenone moiety selected from the group consisting essentially of

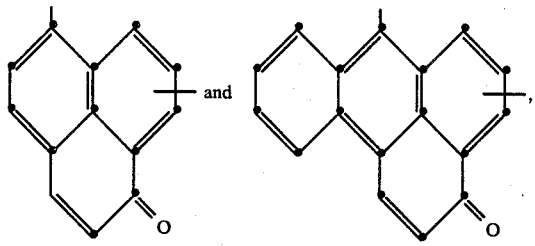

provided that when released as —X—R$^f$—L, —X—R$^f$—L exhibits maximum fluorescent emission at least about 580 nm and maximum absorption above about 530 nm, and L is hydrogen or a specific binding ligand.

7. The composition of claim 6 wherein BLOCK is phosphono, X is —O— and L is hydrogen.

8. An analytical element comprising an absorbent carrier material and containing a hydrolyzable compound represented by the formula:

BLOCK—X—R$^f$—L wherein BLOCK is phosphono, thioxophosphono or a salt thereof, X is —O—, —S— or —NR— wherein R is hydrogen or alkyl, provided that when BLOCK is thioxophosphono, X is —O—, R$^f$ is a phenalenone or benzphenalenone moiety selected from the group consisting essentially of provided that when released as —X—R$^f$—L, —X—R$^f$—L exhibits maximum fluorescent emission at least about 580 nm and a maximum absorption above about 530 nm, and L is hydrogen or a specific binding ligand.

9. The element of claim 8 further comprising a buffer which maintains the pH at 12 or less during an assay.

10. The element of claim 8 further comprising a nonporous support having thereon a porous spreading zone as said absorbent carrier material.

11. The element of claim 8 wherein BLOCK is phosphono, X is —O—, and L is hydrogen.

12. A method for the determination of a phosphatase comprising the steps of:

A. under hydrolyzing conditions, contacting a sample of a liquid suspected of containing a phosphatase with a hydrolyzable compound represented by the formula:

BLOCK—X—R$^f$—L wherein BLOCK is phosphono, thioxophosphono or a salt thereof, X is —O—, —S— or —NR— wherein R is hydrogen or alkyl, provided that when BLOCK is thioxophosphono, X is —O—, R$^f$ is a phenalenone or benzphenalenone fluorescent moiety selected from the group consisting essentially of

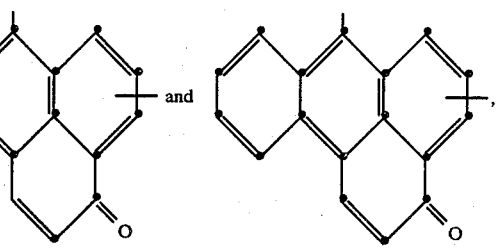

provided that when released as —X—R$^f$—L, —X—R$^f$—L exhibits maximum fluorescent emission at least about 580 nm and maximum absorption above about 530 nm, and L is hydrogen or a specific binding ligand, and B. determining the fluorescent moiety released by hydrolysis as a result of the presence of said phosphatase at a wavelength at least about 580 nm after excitation at a wavelength above about 530 nm.

13. The method of claim 12 for the determination of acid phosphatase carried out at a pH of from about 6 to about 7.

14. The method of claim 12 for the determination of alkaline phosphatase carried out at a pH of from about 8 to about 11.

15. The method of claim 12 which is a competitive binding assay.

16. The method of claim 12 wherein BLOCK is phosphono, X is —O—, and L is hydrogen.

* * * * *